United States Patent [19]
Schmidt et al.

[11] Patent Number: 4,520,821
[45] Date of Patent: Jun. 4, 1985

[54] GROWING OF LONG-TERM BIOLOGICAL TISSUE CORRECTION STRUCTURES IN VIVO

[75] Inventors: Richard A. Schmidt, San Francisco; Emil A. Tanagho, San Rafael, both of Calif.

[73] Assignee: The Regents of the University of California, Berkeley, Calif.

[21] Appl. No.: 373,772

[22] Filed: Apr. 30, 1982

[51] Int. Cl.³ ............................................. A61B 17/00
[52] U.S. Cl. ................................................ 128/334 R
[58] Field of Search ................. 128/1 R, 334 R, 335.5

[56] References Cited

U.S. PATENT DOCUMENTS

| 3,826,241 | 7/1974 | Bucalo | 128/1 R |
| 3,974,526 | 8/1976 | Dardik et al. | 128/334 R |
| 4,137,921 | 2/1979 | Okuzumi et al. | 128/335.5 |
| 4,141,087 | 2/1979 | Shalaby et al. | 128/335.5 X |
| 4,205,399 | 6/1980 | Shalaby et al. | 128/335.5 X |
| 4,243,775 | 1/1981 | Rosensaft et al. | 128/335.5 X |
| 4,304,866 | 12/1981 | Green et al. | 128/1 R X |
| 4,347,847 | 9/1982 | Usher | 128/334 R |

Primary Examiner—C. Fred Rosenbaum
Assistant Examiner—Michelle N. Lester
Attorney, Agent, or Firm—Fliesler, Dubb, Meyer & Lovejoy

[57] ABSTRACT

A mesh or gauze of a bioabsorbable material is used to temporarily correct a defect in a living body. The mesh is of a construction sufficient so that biological tissue in the area of the defect can grow into it and form a long-term biological tissue correction structure before the mesh is completely bioabsorbed. The long-term biological tissue correction structure forms a substantially permanent correction of the defect. The mesh is normally sutured or otherwise fastened in position to correct the defect and is maintained in that position for a time sufficient for the long-term biological tissue correction structure to form and for the mesh to be completely bioabsorbed.

3 Claims, No Drawings

GROWING OF LONG-TERM BIOLOGICAL TISSUE CORRECTION STRUCTURES IN VIVO

DESCRIPTION

1. Technical Field

The invention relates to a method of growing a long-term biological tissue correction structure in vivo and thereby surgically correcting defects in body tissue. More particularly, the invention relates to the particular applicability of such a method to correcting defects in the genitourinary system.

2. Background Art

Prosthesis fashioned from the existing endogenous and exogenous grafts for replacement of smooth muscular parts of the genitourinary tract have the disadvantage of not being sufficiently functional or biocompatible. As a result, better adapted prosthesis are desirable. For example, Peyronie's disease is characterized by localized dense fibrosis of the tunica albuginea of the penis and adjacent cavernous tissue. Many materials have been tried for replacement of the excised tunica albuginea. The earliest was free fat graft used by Lowsley and Boyce, J. Urol., 63:888, 1950; then lyophilized dura matter, Kelami et al, Urology, 6:464, 1975; and rectus sheath, Bruschini et al, Urology, 13:505, 1979; and dermis, Horton et al, Plast. Reconstr. Surg., 52:503, 1973. More recently, testicular tunica vaginalis was tried, Das et al, Invest. Urol., 17:186, 1979; Amin, M., Urologist's Letter Club 36:33, March 1978; Amin et al, J. Urol., 124:815, 1980; and Das, S., J. Urol., 124:818, 1980. Results with the various mentioned material have been varied with the most promising results being obtained with the testicular tunica vaginalis. However, none of the materials have been fully satisfactory. Similar problems occur in other parts of the genitourinary tract.

It would be highly advantageous to provide a prosthesis actually formed of the patient's own biological tissue. It would be further desirable if substantially perfect hemostasis could be attained as well.

The use of bioabsorbable material for structures other than sutures, for example as tubes or sheets for surgical repair, is mentioned in U.S. Pat. No. 3,297,033 of E. E. Schmitt, et al, issued January 10, 1967. In this patent it is mentioned that polyhydroxyacetic esters may be formed as tubes or sheets for surgical repair or may be felted to form absorbable sponges or absorbable gauze. It is also suggested that sheets of the material can be used for tying up and supporting damaged organs and protecting damaged surface areas such as abrasions. This patent does not, however, suggest the use of a gauze or mesh of a bioabsorbable material for such purposes. Further, the patent does not suggest that biological tissue from the area of a defect would grow into such a mesh to form a long-term biological tissue correction structure before the mesh was completely bioabsorbed.

The present invention is directed to overcoming one or more of the problems as set forth above.

DISCLOSURE OF THE INVENTION

The present invention provides a method of growing a long-term biological tissue correction structure in vivo and of thereby sugically correcting a defect in a living entity. The method comprises placing a mesh formed of a bioabsorbable material in position to temporarily correct the defect, the mesh being of a construction sufficient so that biological tissue adjacent to the defect can grow into the mesh and form a long-term biological tissue correction structure before the mesh is completely bioabsorbed. The mesh is normally fashioned in position as a temporary prosthesis as by suturing to correct the defect. It is maintained in position to correct the defect for a time sufficient for the long-term biological tissue correction structure to form and for the mesh to be completely bioabsorbed.

Advantageously, the present invention provides a method of correcting a defect in a living entity by temporarily correcting the defect with a bioabsorbable material, preferably a synthetic bioabsorbable material which can be readily sterilized and handled. It has been experimentally observed that while smooth muscle tissue does not regrow in place, the resulting long-term biological tissue correction structure which exists after the mesh has been completely bioabsorbed provides a highly adequate, and essentially permanent, defect correction. Furthermore, the mesh which serves to temporarily correct the defect has been found to be substantially hemostatic. Thus, trauma is minimized.

BEST MODE FOR CARRYING OUT THE INVENTION

A number of bioabsorbable materials are known. Some of such materials are useful as sutures. For example, catgut is one such useful material. Other useful bioabsorbable materials are discussed in each of U.S. Pat. Nos. 3,297,033 of Schmitt et al, issued Jan. 10, 1967; No. 3,565,077 of Glick, issued Feb. 23, 1971; No. 3,626,948 of, Glick et al, issued Dec. 14, 1971; No. 3,878,284 of Schmitt et al, issued April 15, 1975; No. 4,048,256 of Casey et al, issued Sept. 13, 1977; No. 4,080,969 of Casey et al, issued Mar. 28, 1978; No. 4,095,600 of Casey et al, issued June 20, 1978; No. 4,118,470 of Casey et al, issued Oct. 3, 1978; and No. 4,122,129 of Casey et al, issued Oct. 24, 1978. All of the bioabsorbable materials disclosed in these patents, and any other appropriate non-toxic and non-allergenic biological material which can be readily formed into a mesh or gauze, along with catgut, are usable as the bioabsorbable material of the present invention. Since such materials are well known to the art, and since the present invention is not concerned with any single bioabsorbable material, no long discussion of such materials will be set forth. It should be mentioned, however, that the preferred bioabsorbable materials for use in accordance with the present invention include a polymer selected from polyglycolic acid, its copolymers, and mixtures thereof as are disclosed in the above-mentioned patents.

When the terms "mesh" and "gauze" are used herein they are used to indicate a sheet-like structure having a plurality of holes through it. The mesh or gauze can be of any desired shape, planar, sac-like, tubular, or the like. The shape of the mesh is chosen to best correct any physical defect in the patient. Generally, such meshes may be formed by conventional weaving techniques utilizing conventional bioabsorbable suture material as the thread from which the meshes are woven. However, if desired the mesh can be cast in a single operation, a plurality of holes may be stamped into a sheet of the material, or the mesh may be formed in any other convenient manner.

While the present invention was arrived at during research on genitourinary tract problems, the invention is not limited to such uses. For example, the method of the invention is also useful for surgical treatment of internal organ damage, abrasions, and other problems as well.

In general, the surgeon exposes the defect or damaged area, if it is not naturally exposed as with an abrasion. A mesh is prepared of a size and shape sufficient to bridge, repair and/or reinforce the defect. The mesh is positioned in such a way as to bridge, repair and/or reinforce the defect and is sutured in place as a temporary prosthesis. Where necessary, appropriate wound closure is completed. The mesh is selected to be of a construction sufficient so that biological tissue in the area of the defect can grow into the mesh and form a long-term biological tissue correction structure before the mesh is completely bioabsorbed. The mesh is then retained in position until the long-term biological tissue correction structure forms and the mesh is completely bioabsorbed.

The precise size of the mesh will vary from one usage to another. A mesh made from the material Dexon (a trademark of American Cyanamid Co.) was woven from 308 denier-thick polyglycolic acid sutures with transverse intersections of polypropylene 4/0 as marking fibers. This mesh proved very satisfactory for treatment of both urethral defects and Peyronie's disease. The particular size of the mesh is not critical. However, it is critical that the mesh be of a sufficient size so that it will serve as a temporary prosthesis for the time necessary for the adjacent biological tissue to grow into it and form a long-term biological tissue correction structure. The mesh should also not be so large that bioabsorption will take an undue period of time. Many years of experience with absorbable tissues has led to the selection of a range of sizes for these sutures. Meshes woven from sutures of such sizes are, generally, quite suitable for use in practicing the present invention. The surgeon would use his skill in selecting the particular size mesh most appropriate for any particular defect correcting operation.

The size of the holes in the mesh will generally be selected so that the temporary correction of the defect performed by the mesh will be substantially hemostatic.

It is possible to utilize the present invention partially in vitro and partially in vivo. Cellular material can be removed from the area of the defect, for example, a defect in the genitourinary tract, and cultured in vitro on a sample of the mesh which is suitable for eventual temporary correction of the defect. In this manner, biological tissue from the area of the defect can be grown into the mesh outside of the body. The mesh along with the biological tissue can then be used to temporarily correct the defect. Further cell growth takes place after implantation and the bioabsorbable material is eventually absorbed. To date, it has not been possible to carry out this procedure with smooth muscle tissues and have the smooth muscle tissues not deteriorate after implantation in the body. Still, such implantations have been successful in that epithelial cells, endothelial cells and fibroblasts can survive such implantations.

The invention will be better understood by reference to the following examples:

EXAMPLE 1

Preparation of Dexon Mesh

A Dexon mesh was woven from 308 denier-thick polyglycolic acid sutures obtained from Davis and Geck of Danbury, CT. The mesh was made with transverse intersections of polypropylene 4/0 as marking fibers. The mesh was sterilized in ethylene oxide for 12 hours and was then aired for 24 hours before use.

EXAMPLE 2

Use of Mesh for Treating Urethral Strictures

A Dexon mesh made as described in Example 1 was used for grafting urethral defects in seven mongrel male dogs. The ventral half of the urethral circumference with its investing corpus spongiosum was excised from each of the dogs for a length of 3-4 cm. The Dexon mesh was sutured to the defective area. A perineal urethrotomy was established and no splints were left behind.

The dogs were studied between two and six months. Retrograde urethrography showed that the operative area healed without strictures or irregularities. Intravenous urography showed no back pressure effects and cultured urine was always sterile. Histologic examination two months after surgery showed that the urothelium was completely healed without inflammatory changes or disruption. The suburothelial tissues were replaced by dense collagenous connective tissue in a regular way. The excised corpus spongiosum did not regenerate. After six months, the area of dense collagen was diminished in size so that the operative area could hardly be identified except by the absence of corpus spongiosum. The dogs were sacrificed, one at two months, two at three months, two at four months, one at five months, and one at six months for detailed studies. The penis was removed and immersed in a 10 percent phosphate-buffered formalin solution for one week to fix the tissues. The operated area and a control area were studied by light microscopy after being stained with hematoxylin and eosin, Masson's trichrome stain, and Van Gieson's elastin stain. Sections from both operated and nonoperated areas were examined to provide an internal control for each dog. The Dexon mesh was incompletely absorbed after two months but appeared to be completely absorbed after three months.

EXAMPLE 3

Use of Mesh to Surgically Manage Peyronie's Disease

Six male mongrel dogs weighing 18-25 kg each were anesthetized by pentobarbital (25 mg/kg of body weight). An incision 5 cm long was made in the skin covering the body of the penis and an area of 1.5 cm by 2.5 cm of tunica albuginea covering the dorsum of the organ was excised, exposing underlying cavernous tissue. The resulting defect was grafted with a Dexon mesh of the same dimensions and made in accordance with Example 1. The mesh was sutured in place by continuous 3/0 Dexon suture. Some silk sutures were also used to facilitate later identification of the graft.

One dog was studied three weeks after operation, one at two months, two after four months, and two after six months. Under pentobarbital anesthesia artificial erection was created by injection of radiopaque fluid (meglumine diatrizoate) into the corpora. Two exposures in the anteroposterior and lateral views were obtained to diagnose patency or obstruction of the cavernous tissue, bulge of the grafted area, or curvature of the penis. The dogs were sacrificed. The whole skin overlying the penis was incised, the graft area identified and examined and the penis removed and dropped in 10 percent phosphate-buffered formalin for one week to fix the tissues. The grafted area was then examined histologically after staining (hematoxylin and eosin stain, Masson trichrome stain and Verhoff Van Geison's elastic stain).

None of the dogs developed post-operative complications. After four months the grafted area had the same consistency as the intact area and no induration could be recognized. On macroscopic examination of the tunica albuginea after three weeks the grafted area could be identified because healing was not yet complete. After four and six months the grafted area could not be identified (except by the nonabsorbable marking sutures) because it looked the same as the non-grafted area. Artifically induced erection revealed no bulge of the grafted area or deformity of the organ. Cavernosography (anteroposterior and lateral views) substantiated these results and proved patency of the cavernous tissue.

Histologic examination three weeks after operation showed the defective area of the tunica albuginea with some bridges of collagen between the cut edges and imcompletely absorbed mesh. At four and six months the graft area was completely healed and uniformly continuous with the neighboring collagenous tissue, with no untoward cellular reaction. There was no hyalinization of collagen fibers. The initial inflammatory cell response was reduced to local foreign body reaction containing the nonabsorbable sutures.

The polyglycolic acid suture mesh material was found to be ideal for grafting defects resulting from excision of Peyronie's plaques. Perfect hemostatis and absorption was observed, leaving a perfectly healed tunica albuginea without cavernous tissue obstruction, bulge or deformity.

Industrial Applicability

The present invention is applicable to the correction of defects in humans and animals.

Other aspects, objectives, and advantages of the present invention can be obtained from a study of the disclosure and the appended claims.

We claim:

1. A method of growing a long-term biological tissue correction structure in vivo and of thereby surgically correcting a defect in a living body, comprising:
   removing biological tissue from the area of the defect;
   growing the removed biological tissue in vitro on a mesh formed of a bioabsorable material;
   placing the mesh in position to temporarily correct the defect, the mesh, when placed in position to correct the defect, including biological tissue grown thereon in vitro, being of a construction sufficient so that biological tissue in the area of the defect can grow into the mesh and form a long-term biological tissue correction structure before the mesh is completed bioabsorbed and of a size selected to form a hemostatic temporary correction of the defect;
   fastening the mesh in position to correct the defect; and
   maintaining the mesh in position to correct the defect for a time sufficient for the long-term biological tissue correction structure to form and for the mesh to be completely bioabsorbed.

2. A method as set forth in claim 1, wherein the bioabsorbable material includes a polymer selected from polyglycolic acid, its copolymers, and mixtures thereof.

3. A method as set forth in claim 1, wherein said defect is in the genitourinary tract.

* * * * *